United States Patent
Davis et al.

(10) Patent No.: US 10,234,417 B2
(45) Date of Patent: Mar. 19, 2019

(54) SENSOR INTERROGATION WITH FAST RECOVERY

(71) Applicant: MSA TECHNOLOGY, LLC, Cranberry Township, PA (US)

(72) Inventors: Brian Keith Davis, Butler, PA (US); Michael Alvin Brown, Cranberry Township, PA (US); Jerin Miller, Pittsburgh, PA (US); Ryan Alan Sherry, Cranberry Township, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 251 days.

(21) Appl. No.: 15/012,919

(22) Filed: Feb. 2, 2016

(65) Prior Publication Data
US 2017/0219515 A1    Aug. 3, 2017

(51) Int. Cl.
| | |
|---|---|
| *G01N 27/407* | (2006.01) |
| *G01N 27/404* | (2006.01) |
| *G01N 33/00* | (2006.01) |

(52) U.S. Cl.
CPC ....... *G01N 27/4074* (2013.01); *G01N 27/404* (2013.01); *G01N 27/4073* (2013.01); *G01N 33/0006* (2013.01)

(58) Field of Classification Search
None
See application file for complete search history.

(56) References Cited

U.S. PATENT DOCUMENTS

| | | | |
|---|---|---|---|
| 4,189,367 A | | 2/1980 | Connery |
| 5,202,637 A | * | 4/1993 | Jones ............... G01N 27/404 204/401 |
| 6,096,186 A | * | 8/2000 | Warburton ......... G01N 33/007 204/401 |
| 6,896,781 B1 | | 5/2005 | Shen |
| 7,413,645 B2 | | 8/2008 | Scheffler |
| 8,097,146 B2 | | 1/2012 | Smith |
| 9,057,690 B2 | | 6/2015 | Smith |

FOREIGN PATENT DOCUMENTS

| | | | | |
|---|---|---|---|---|
| DE | 3809107 | * | 9/1989 | ......... G01N 33/0006 |
| DE | 3809107 A1 | | 9/1989 | |
| EP | 0628810 A2 | | 12/1994 | |
| WO | WO9221962 A1 | | 12/1992 | |
| WO | WO2017136407 A1 | | 8/2017 | |

OTHER PUBLICATIONS

Cao, Z. and Stetter, J.R., "The Properties and Applications of Amperometric Gas Sensors," Electroanalysis, 4(3), 253 (1992).

* cited by examiner

*Primary Examiner* — Gurpreet Kaur
*Assistant Examiner* — Steven E Rosenwald
(74) *Attorney, Agent, or Firm* — Bartony & Associates, LLC

(57) ABSTRACT

A method of operating a sensor to detect an analyte in an environment, wherein the sensor includes a working electrode and circuitry in operative connection with the working electrode, includes performing a sensor interrogation cycle including applying electrical energy to the working electrode to generate a non-faradaic current, measuring a response to the generation of the non-faradaic current to determine a state of the sensor, and actively controlling the circuitry to dissipate the non-faradaic current.

30 Claims, 9 Drawing Sheets

SENSOR INTERROGATION WITH FAST RECOVERY

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Prudence dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually the target gas or analyte gas the instrument is intended to detect); b) collecting and interpreting the sensor response; and c) indicating to the end user the functional state of the system (that is, whether or not the instrument is properly functioning).

Such bump tests are performed regularly and, typically, daily. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is being interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities such as industrial facilities that include many gas detection systems or instruments. The bump check also requires the use of expensive and potentially hazardous calibration gases. Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment.

Recently, a number of systems and methods have been proposed to reduce the number of bump tests required. Such a system may, for example, include electronic interrogation of a sensor. A sensor is offline or unable to sense an anlayte or target gas or gases during such electronic interrogation. For example, a number of sensors include functionality to electronically interrogate of one or more electrodes thereof, require a user to initiate an interrogation process which takes between 20-30 seconds. For example, a potential change may be applied to an electrode for 5-10 seconds and the corresponding current decay curve is studied over a 20-30 second period. As set forth above, during such a 20-30 second period, the sensor is offline and can't be used to sense the analyte(s). It is desirable to minimize the amount of time a sensor is offline, particularly in cases wherein a sensor is used to detect one or more hazardous analytes or target gases.

SUMMARY

A method of operating a sensor to detect an analyte in an environment, wherein the sensor includes a working electrode and circuitry in operative connection with the working electrode, includes performing a sensor interrogation cycle including applying electrical energy to the working electrode to generate a non-faradaic current, measuring a response to the generation of the non-faradaic current to determine a state of the sensor, and actively controlling the circuitry to dissipate the non-faradaic current. In a number of embodiments, the sensor interrogation cycle lasts less than one second. The method may, for example, include periodically initiating the sensor interrogation cycle.

Applying electrical energy to the working electrode may, for example, include applying a first potential difference to the working electrode. Actively controlling the circuitry may, for example, include applying at least a second potential difference to the working electrode of opposite polarity to the first potential difference.

In a number of embodiments, actively controlling the circuitry includes decreasing a load resistance in electrical connection with the working electrode. Applying electrical energy to the working electrode may, for example, include changing the potential of the working electrode for a period of time. The period of time may, for example, be no greater than $\frac{1}{2}$ seconds, no greater than $\frac{1}{16}$ seconds, or no greater than $\frac{1}{64}$ seconds. In a number of embodiments, decreasing the load resistance occurs at the same time or after measuring the response.

In a number of embodiments, the sensor comprises a load resistor and a bypass switch to bypass the load resistor. The bypass switch may, for example, include a field effect transistor switch, wherein activating a field effect transistor switch decreases the load resistance and deactivating the field effect transistor switch increases the load resistance.

In a number of embodiments, the method further includes adjusting the output of the sensor at least in part on the basis of the sensor interrogation cycle.

An electrochemical sensor is operable to detect an analyte in an environment during an operational mode of the sensor and includes a working electrode and circuitry in operative connection with the working electrode, which is adapted to carry out an electronic interrogation cycle. The circuitry includes a power source via which electrical energy is applied to the working electrode during the electronic interrogation cycle to generate a non-faradaic current. The electrochemical sensor further includes a system to measure a response of the sensor and a control system to actively control the circuitry to dissipate the non-faradaic current. In a number of embodiments, the circuitry is adapted to complete the sensor interrogation cycle in less than one second. The circuitry may, for example, be adapted to periodically initiate the sensor interrogation cycle.

The circuitry may, for example, be adapted to apply a first potential difference to the working electrode. The control system may, for example, actively control the circuitry to apply at least a second potential difference to the working electrode of opposite polarity to the first potential difference to dissipate the non-faradaic current. The control system may, for example, decrease a load resistance in electrical connection with the working electrode to dissipate the non-faradaic current. Decreasing the load resistance may, for example, occur at the same time or after measuring the response to the generation of the non-faradaic current.

Applying electrical energy to the working electrode may, for example, include changing the potential of the working electrode for a period of time. In a number of embodiments, the period of time is no greater than ½ seconds, no greater than $1/16$ seconds, of no greater than $1/64$ seconds.

In a number of embodiments, the circuitry include a load resistor and a bypass switch to bypass the load resistor. The bypass switch may, for example, include a field effect transistor switch. Activating the field effect transistor switch may, for example, decrease the load resistance and deactivating the field effect transistor switch may, for example, increase the load resistance.

In a number of embodiments, the control system is further adapted to adjust output of the sensor at least in part on the basis the sensor interrogation cycle.

A method of operating a sensor operable to detect an analyte in an environment, wherein the sensor includes a working electrode and circuitry in operative connection with the working electrode, includes performing a sensor interrogation cycle including applying electrical energy to the working electrode to generate a non-faradaic current and measuring a response to the generation of the non-faradaic current to determine a state of the sensor. In a number of embodiments, the amount of energy applied is low enough in amplitude and short enough in duration such that the non-faradaic current dissipates quickly enough so that a baseline current is reached less than one second from application of the electrical energy at which an analytic response of the sensor can be measured to detect the analyte.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
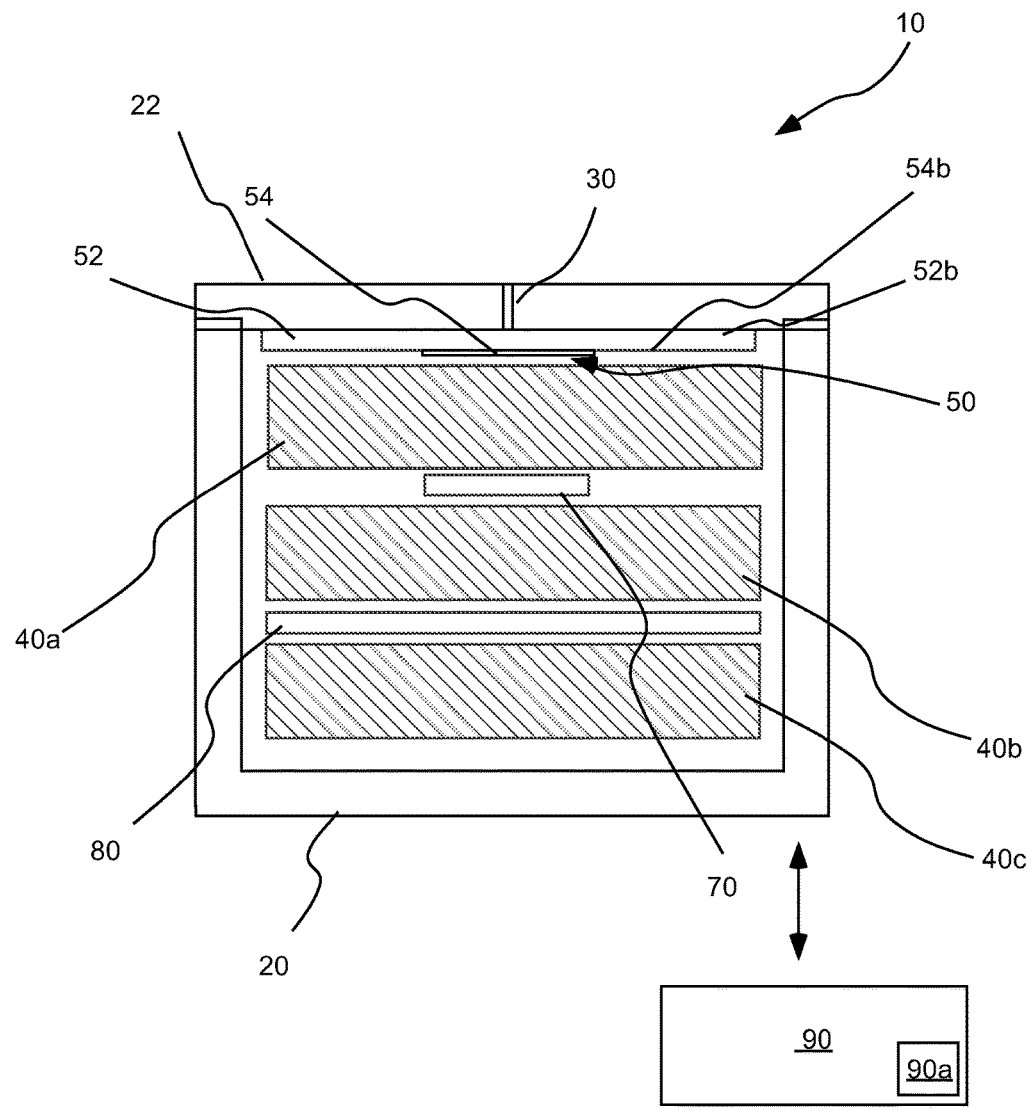
FIG. 1A illustrates schematically an embodiment of an electrochemical sensor hereof.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of the embodiments hereof. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an electrode" includes a plurality of such electrodes and equivalents thereof known to those skilled in the art, and so forth, and reference to "the electrode" is a reference to one or more such electrodes and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

As used herein, the term "circuit" or "circuitry" includes, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software.

The term "control system" or "controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

The term "processor," as used herein includes, but is not limited to, one or more of virtually any number of processor systems or stand-alone processors, such as microprocessors, microcontrollers, central processing units (CPUs), and digital signal processors (DSPs), in any combination. A processor may be associated with various other circuits that support operation of the processor, such as a memory system (for example, random access memory (RAM), read-only memory (ROM), programmable read-only memory (PROM), erasable programmable read only memory (EPROM)), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

As described above, it is desirable to minimize the amount of time a sensor is offline to conduct sensor testing diagnostics (that is, during a sensor interrogation cycle). In a number of embodiments, devices, systems and/or methods described herein generally allow for a return to a normal mode operation for the electrochemical sensors hereof that is under 10 seconds, under 5 seconds or even under 1 second. The devices, systems and methods hereof not only allow an instrument including one or more sensor to remain "online", but also provide for active, automatic sensor status monitoring as a background operation, without the requirement of user initiation. The frequency of the interrogations hereof may vary. Providing for sensor interrogation at a frequency of, for example, several times an hour can provide for nearly constant sensor life and health status monitoring.

In an electrochemical gas sensor, the gas to be measured typically passes from the surrounding atmosphere or environment into a sensor housing through a gas porous or gas permeable membrane to a first electrode or working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working electrode. A comprehensive discussion of electrochemical gas sensors is also provided in Cao, Z. and Stetter, J. R., "The Properties and Applications of Amperometric Gas Sensors," *Electroanalysis,* 4(3), 253 (1992), the disclosure of which is incorporated herein by reference.

The working and counter electrode combination produces an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through the electrolyte. Functions of the electrolyte include: (1) to efficiently carry the ionic current; (2) to solubilize the analyte gas; (3) to support both the counter and the working electrode reactions; and (4) to form a stable reference potential with the reference electrode. Criteria for an electrolyte may, for example, include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction (a redox) reaction occurs to provide a mechanism whereby the ionic conduction of the electrolyte solution is coupled with the electron conduction of the electrode to provide a complete circuit for a current. The measurable current arising from the cell reactions of the electrochemical cell is directly proportional to the extent of reaction occurring at the electrode. Preferably, therefore, a high reaction rate is maintained in the electrochemical cell. For this reason, the counter electrode and/or the working electrode of the electrochemical cell generally include an appropriate electrocatalyst on the surface thereof to support the reaction rate.

As a result of electrostatic forces, the volume of solution very close to the working electrode surface is a very highly ordered structure. This structure is important to understanding electrode processes. The volume of solution very close to the electrode surface is variously referred to as the diffusion layer, diffuse layer, and or the Helmholtz layer or plane.

The magnitudes of the resistance and capacitance present in an electrochemical cell are a result of the nature and identities of the materials used in its fabrication. The resistance of the electrolyte is a result of the number and types of ions dissolved in the solvent. The capacitance of the electrode is primarily a function of the effective surface area of the electrocatalyst. In an ideal world, these quantities are invariant. However, the solution resistance present in an amperometric gas sensor that utilizes an aqueous (water-based) electrolyte may change, for example, as a result of exposure to different ambient relative humidity levels. As water transpires from the sensor, the chemical concentration of the ionic electrolyte increases. This concentration change can lead to increases or decreases in the resistivity of the electrolyte, depending on the actual electrolyte used.

Moreover, even for substances normally thought of as insoluble in a particular solvent, there is a small, but finite concentration of the substance in the solvent. For example, there is a very small, but finite concentration of metal from the electrodes dissolved in the electrolyte of an electrochemical sensor. This small concentration of dissolved metal is constantly in flux. That is, metal atoms are constantly dissolving from the electrode and then replating somewhere else. The net effect of this process is to decrease the effective surface area of the electrode. This has the effect of lowering the sensor capacitance over time. Both of the above-described effects have the net effect of changing the sensitivity of the sensor over its lifetime.

FIG. 1A illustrates a schematic diagram of a representative embodiment of an electrochemical sensor 10 used in the studies hereof. Sensor 10 includes a housing 20 having a gas inlet 30 for entry of one or more target gases or analyte gases into sensor 10. In the illustrated embodiment, electrolyte saturated wick materials 40a, 40b and 40c separate a working electrode 50 from a reference electrode 70 and a counter electrode 80 within sensor 10 and/or provide ionic conduction therebetween via the electrolyte absorbed therein. Electronic circuitry 90 as known in the art is provided, for example, to maintain a desired potential difference between working electrode 50 and reference electrode 70, to vary or pulse the potential difference as described herein, and to process an output signal from sensor 10. Electronic circuitry 90 may include or be in operative connection with a controller 90a such as a microprocessor to control various aspects of the operation of sensor 10.

In the illustrated embodiment, working electrode 50 may be formed by, for example, depositing a first layer of catalyst 54 on a first diffusion membrane 52 (using, for example, catalyst deposition techniques known in the sensor arts). Working electrode 50 may be attached (for example, via heat sealing) to an inner surface of a top, cap or lid 22 of housing 20.

Figure 1B:
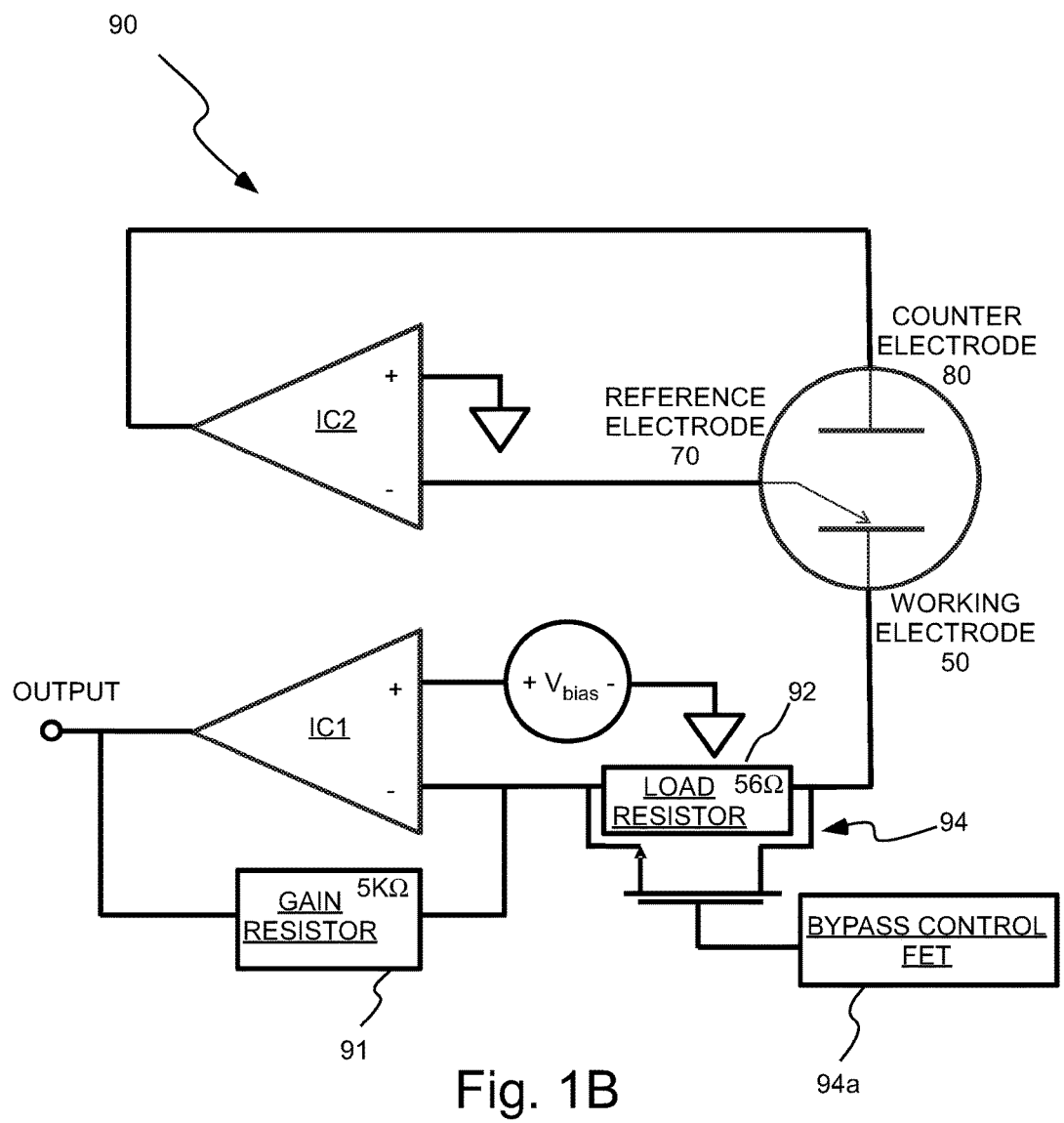
FIG. 1B illustrates a schematic circuit diagram of an embodiment of a sensor hereof.

FIG. 1B illustrates schematically an embodiment of a portion or part of electronic or control circuitry 90 used in a number of studies of the sensors hereof. Such electronic circuitry is sometimes referred to as a potentiostatic circuit. In a three-electrode sensor as illustrated in FIG. 1A, a predetermined potential difference or voltage is maintained between reference electrode 70 and sensing or working electrode 50 to control the electrochemical reaction and to deliver an output signal proportional to the current produced by the sensor. As described above, working electrode 50 responds to the analyte or target gas by either oxidizing or reducing the gas. The redox reaction creates a current flow that is proportional to the gas concentration. Current is supplied to sensor 10 through counter electrode 80. A redox reaction opposite to that of the reaction at the working electrode takes place at counter electrode 80, completing the circuit with working electrode 50. The potential of counter electrode 80 is allowed to float. When gas is detected, the cell current rises and counter electrode 80 polarizes with respect to reference electrode 70. The potential on counter electrode 80 is not important, as long as the circuit provides sufficient voltage and current to maintain the correct potential of working electrode 50.

The measuring circuit for electrical circuitry 90 includes a single stage operational amplifier or op amp IC1. The sensor current is reflected across a gain resistor 91 (having a resistance of 5 k$\Omega$ in the illustrated embodiment), generating an output voltage. A load resistor 92 (having a resistance of 56$\Omega$ in the illustrated embodiment) may be chosen, for example, via a balance between the fastest response time and best signal-to-noise ratio.

A control operational amplifier IC2 provides the potentiostatic control and provides the current to counter electrode 80 to balance the current required by working electrode 50. The inverting input into IC2 is connected to the reference electrode, but does not draw any significant current from the reference electrode.

During electronic interrogation of a sensor hereof such as sensor 10, a non-faradaic current is induced (for example, via application of energy to working electrode 50). For example, a step change in potential may be created which generates a non-faradaic current. The generated non-faradaic current can be used to monitor the sensor functionality or health as a result of the charging of the electrodes. However, as described above, the sensor should be returned to its normal bias potential or potential range for normal operation in sensing a target or analyte gas. The process of returning the sensor to its operating bias or operating potential difference (which may be zero) produces a current peak (a charge build-up) in the opposite direction. The current peak arising on return to the operating potential difference can take many of seconds to dissipate.

The present inventors have discovered that information regarding sensor health or the state of the sensor may be obtained upon application of energy/electrode potential changes that are quite small and/or short in duration, and measuring/analyzing single data points or multiple data points over short time spans in a resultant response/current curve. Moreover, the present inventors have discovered that a rapid discharge of even relatively large current peaks arising when inducing a non-faradaic current in sensor 10 (or another sensor hereof) and/or in returning sensor 10 (or another sensor hereof) to its operating potential difference may be achieved via active control of sensor electronics 90 (for example, by decreasing a load resistance in electronic circuitry 90 between working electrode 50 and the point at which the output/response is measured after the test potential difference has been applied). In a number of embodiments, the load resistance between working electrode 50 and the output of operational amplifier IC1 is decreased to a low value. Subsequently, the load resistance between working electrode 50 and the output of operational amplifier IC1 is restored to its normal or operational load resistance (or to within an operation range of load resistance) after the charge is substantially dissipated or fully dissipated.

In a number of embodiments, load resistor 92 (see FIG. 1B) is bypassed to decrease the load resistance between working electrode 50 and the inverting terminal of operational amplifier IC1. A bypass circuit 94 may, for example, be provided to bypass load resistor 92. In a number of embodiments, a field effect transistor (FET) 94a was used as a switch in a bypass circuit 94 to controllably effect a bypass or short circuit around load resistor 92. In a number of embodiments, a metal-oxide-semiconductor FET or MOSFET was used.

Figure 2A:
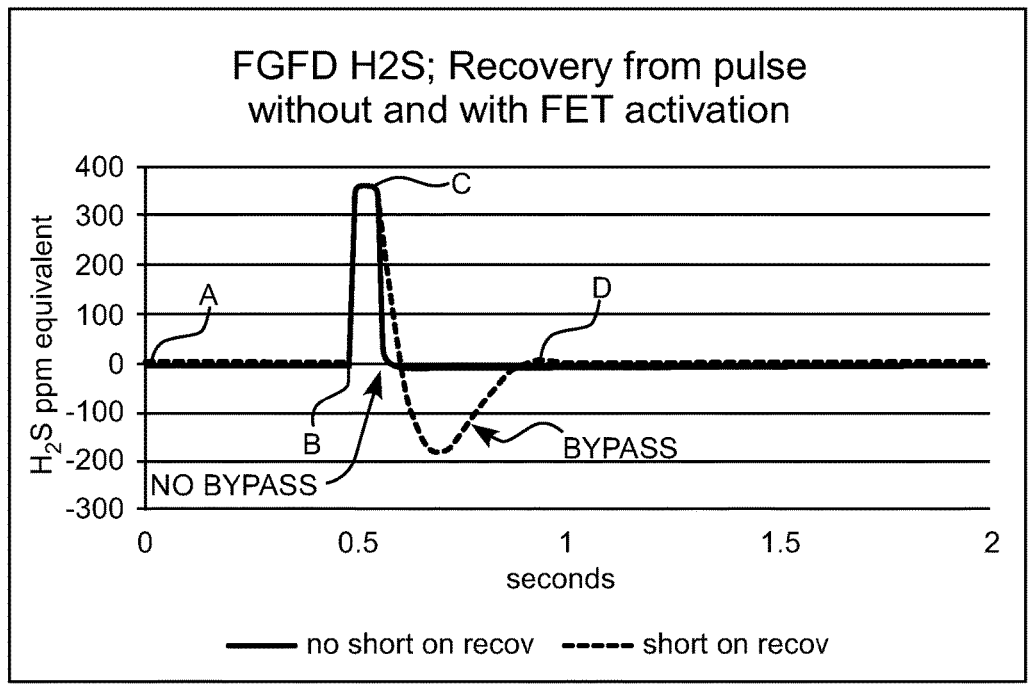
FIG. 2A illustrates recovery of a sensor signal of a sensor for hydrogen sulfide ($H_2S$) after imposition of a $1/16^{th}$ second +10 mV pulse for the case in which a load resister of a predetermined resistance is in series with the working electrode and for the case that the resister is bypassed or short circuited via an FET switch at the end of the pulse.
Figure 2B:
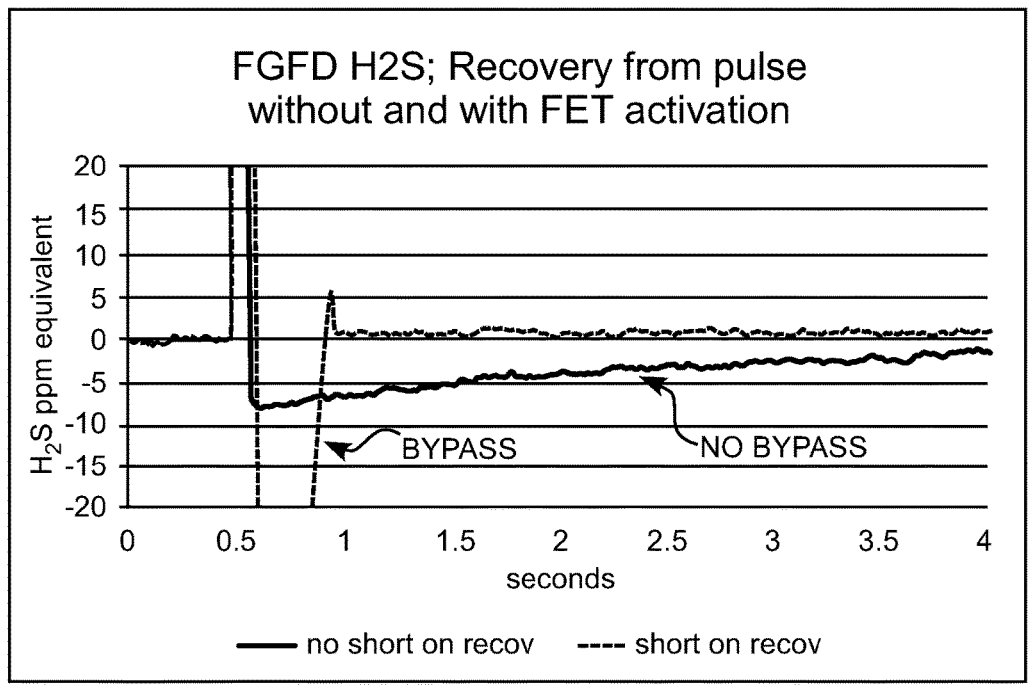
FIG. 2B illustrates a portion of the results of FIG. 2A over expanded output and time scales.
Figure 3A:
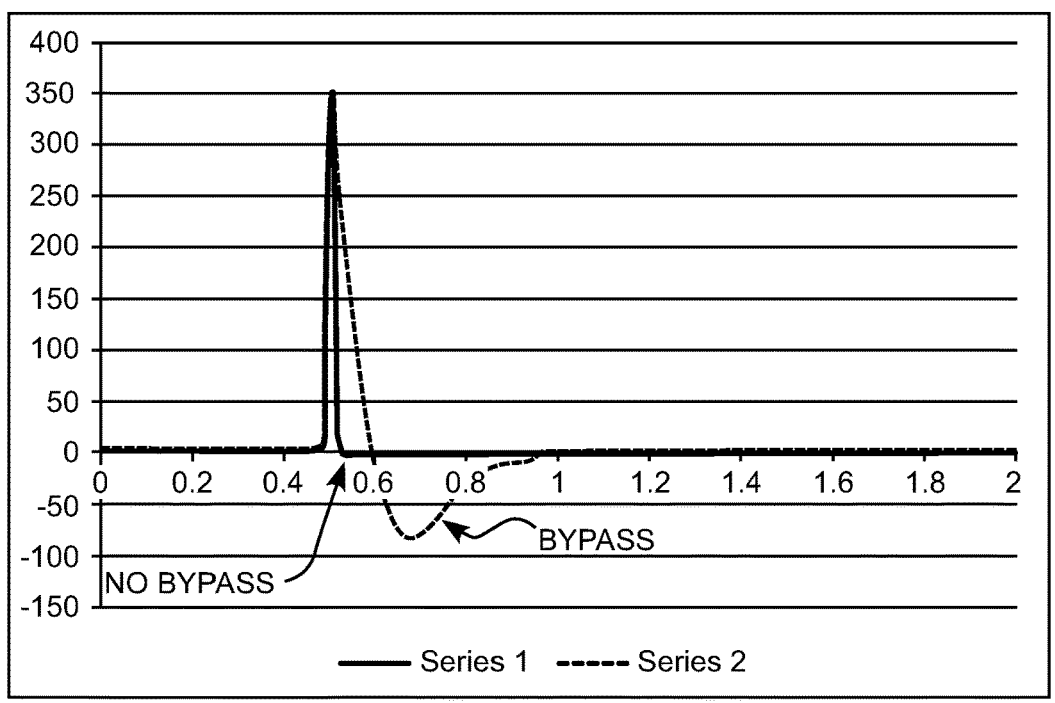
FIG. 3A illustrates recovery of a sensor signal of a sensor for hydrogen sulfide ($H_2S$) after imposition of a $1/64^{th}$ second +10 mV pulse for the case in which a load resister of a predetermined resistance is in series with the working electrode and for the case that the resister is bypassed or short circuited via an FET switch at the end of the pulse.
Figure 3B:
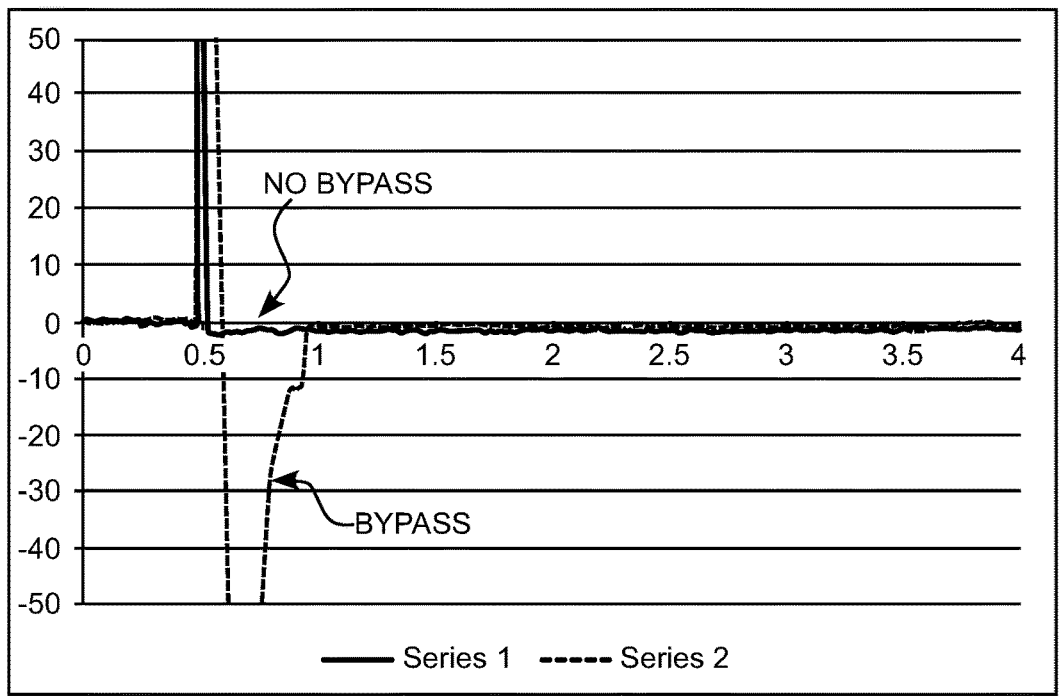
FIG. 3B illustrates a portion of the results of FIG. 3A over expanded output and time scales.

FIGS. 2A and 2B illustrate the output of sensor 10 including a working electrode 50 designed to detect hydrogen sulfide or $H_2S$. In the studied embodiment of FIGS. 2A and 2B, working electrode 50 was formed by depositing an iridium catalyst on a diffusion membrane, reference electrode 70 was formed by depositing an iridium catalyst on a diffusion membrane, and counter electrode 80 was formed by depositing an iridium catalyst on a diffusion membrane. The bias potential or operating potential difference of the sensor was 0 mV. As illustrated in FIG. 2A, at a time represented by point A, an electronic interrogation procedure is initiated. After 0.5 seconds (represented by point B), a test potential difference is applied. In the illustrated studies, a test potential of +10 mV was applied. A measured peak value (MPV) of output was recorded $1/16^{th}$ of a second after application of the test potential as represented by point C. At that time, the potential was also returned to the operating potential difference of 0 mV. FIG. 2A illustrates the sensor output when load resistor 92 is bypassed by activation of FET 94a and the sensor output when load resistor 92 is not bypassed. In the case where load resistor 92 is bypassed, FET 94a was activated at generally the same time or contemporaneously with return of the potential to the operating potential difference. As illustrated in FIG. 2A, the significantly lower load resistance causes a significantly greater negative current spike (which would be viewed as a very high negative gas ppm reading in the normal mode of operation) than the case in which load resistor 92 is not bypassed. It was, therefore, surprising that the rapid discharge which occurs upon bypassing load resistor 92 returns the sensor output to the baseline in a very short period of time (that is, in less than 1 second). The contrast with the case in which load resistor 92 is not bypassed is best illustrated in FIG. 2B in which the output scale is expanded. As illustrated in FIG. 2B, the output returns to the baseline output in less than one second (that is, from t=0.5 seconds to t≈0.95 seconds) when load resistor 92 is bypassed, whereas it takes many seconds for the output to return to the baseline output when load resistor 92 is not bypassed. As illustrated in FIG. 2A, when FET 94a is deactivated and 56Ω load resistor 92 is restored in the circuit at a time of approximately 0.95 seconds as represented by point D, the output current is below a value that would be discerned by the end user. This value is typically in the range of approximately 0 to ±2 ppm of the target gas FIGS. 3A and 3B illustrate the output of the $H_2S$ sensor when a test potential of +10 mV is applied for $1/64^{th}$ of a second. Approximately 0.5 seconds after initiation of the test procedure at t=0, a test potential difference of +10 mV is applied. The peak output value was recorded $1/64^{th}$ of a second after application of the test potential. At that time, the potential difference was also returned to the operating potential difference of 0 mV. FIG. 3A illustrates both the sensor output when load resistor 92 is bypassed by activation of FET 94a, and the sensor output when load resistor 92 is not bypassed. In the case where the load resistor is bypassed, FET 94a was activated at generally the same time or contemporaneously with return of the potential to the operating potential difference. Once again, the significantly lower load resistance causes a significantly greater negative current spike (that would viewed as a very high negative gas ppm reading in the normal mode of operation) than the case in which load resistor 92 is not bypassed. The contrast with the case in which load resistor 92 is not bypassed is best illustrated in FIG. 3B in which the output scale is expanded. As illustrated in FIG. 3B, similar to the results illustrated in FIG. 2B, although the output returns to the baseline output in less than one second when load resistor 92 is bypassed, it takes many seconds for the output to return to the baseline output when load resistor 92 is not bypassed (FIG. 3B). The 56Ω load resistor 92 was restored in the circuit at a time of less than 1 second from the initiation of the test procedure.

Figure 4A:
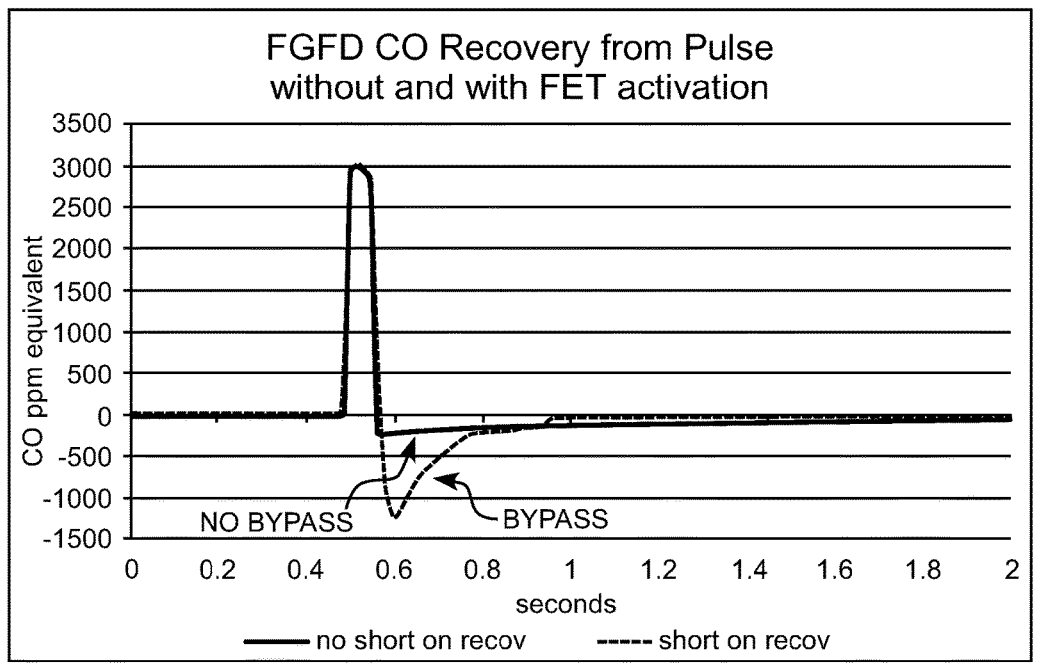
FIG. 4A illustrates recovery of a sensor signal of a sensor for carbon monoxide (CO) after imposition of a $1/16^{th}$ second +10 mV pulse for the case in which a load resister of a predetermined resistance is in series with the working electrode and for the case that the resister is bypassed or short circuited via an FET switch at the end of the pulse.
Figure 4B:
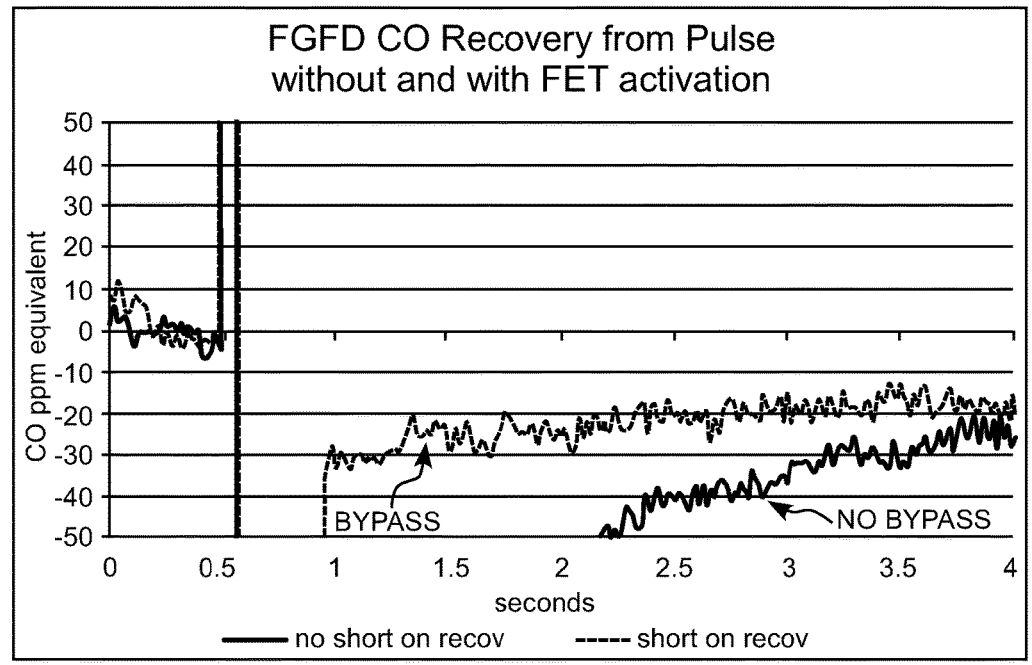
FIG. 4B illustrates a portion of the results of FIG. 4A over expanded output and time scales.
Figure 5A:
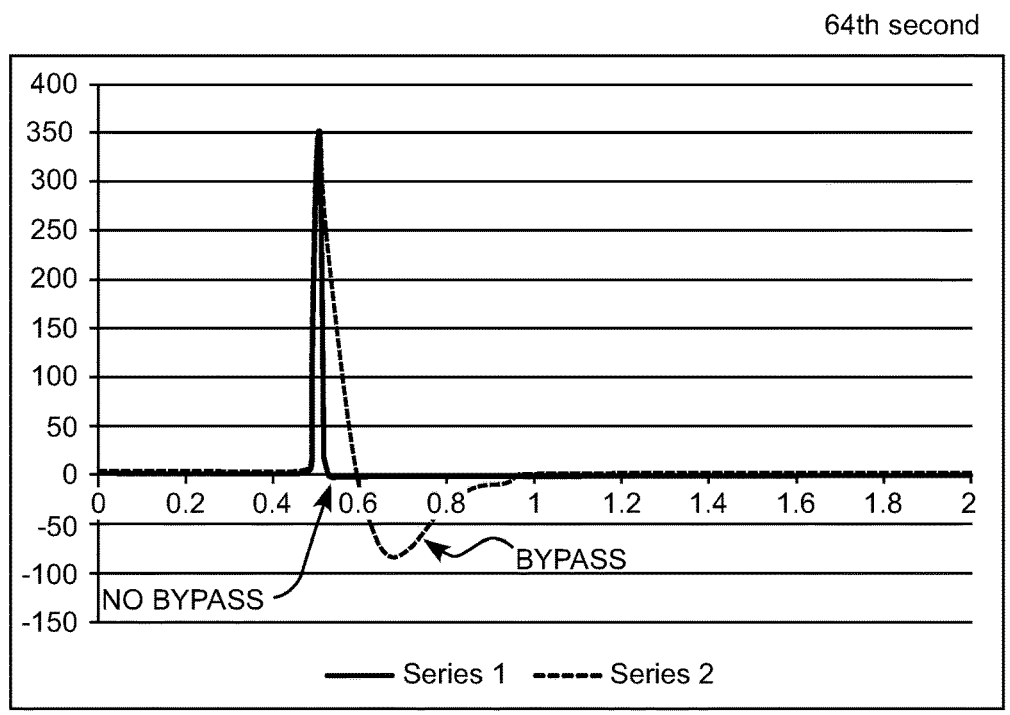
FIG. 5A illustrates recovery of a sensor signal of a sensor for carbon dioxide after imposition of a $1/64^{th}$ second +10 mV pulse for the case in which a load resister of a predetermined resistance is in series with the working electrode and for the case that the resister is bypassed or short circuited via an FET switch at the end of the pulse.
Figure 5B:
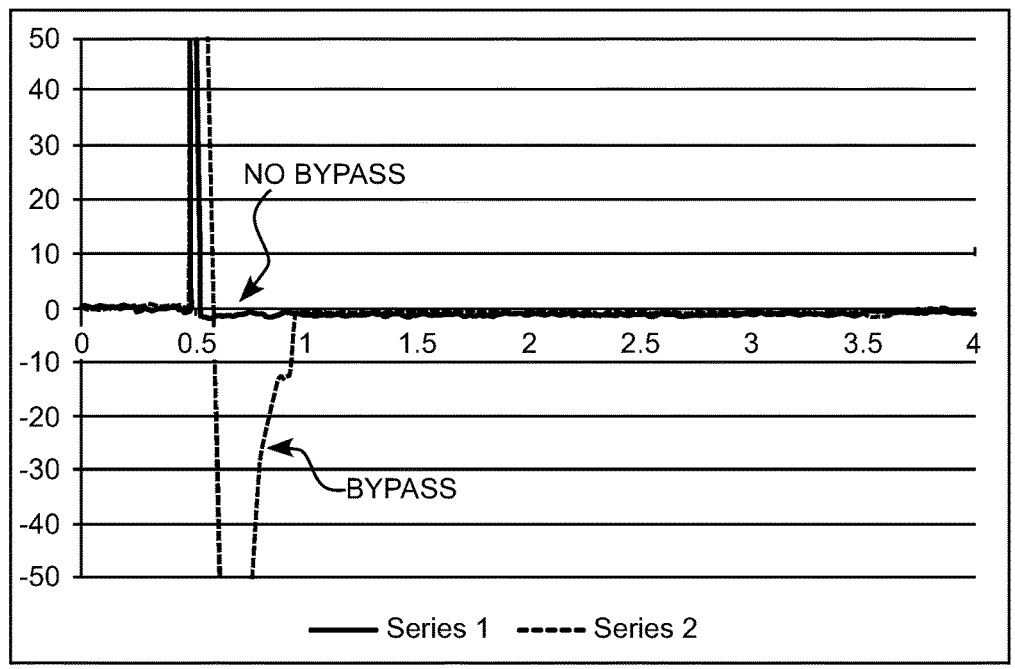
FIG. 5B illustrates a portion of the results of FIG. 5A over expanded time and output scales.

FIGS. 4A and 4B illustrate the output of sensor 10 including a working electrode 50 designed to detect carbon monoxide or CO in response to a +10 mV test potential difference lasting for $1/16^{th}$ of a second. In the studied embodiment of FIGS. 2A and 2B, working electrode 50 was formed by depositing an platinum catalyst on a diffusion membrane, reference electrode 70 was formed by depositing an platinum catalyst on a diffusion membrane, and counter electrode 80 was formed by depositing an platinum catalyst on a diffusion membrane. The bias potential or operating potential difference of the sensor was 180 mV. Similar to the studies described in connection with FIGS. 2A and 2B, approximately 0.5 seconds after initiation of the test procedure at t=0, a test potential difference of +10 mV is applied. The peak output value was recorded $1/16^{th}$ of a second after application of the test potential and the potential difference was returned to the operating potential difference of 180 mV. FIG. 4A illustrates sensor output when load resistor 92 is bypassed by activation of FET 94a and sensor output when load resistor 92 is not bypassed. In the case wherein load resistor 92 is bypassed, FET 94a was activated at generally the same time or contemporaneously with return of the potential to the operating potential difference. As with the $H_2S$ sensors studied in connection with FIGS. 2A through 3B, the significantly lower load resistance causes a significantly greater negative current spike than is the case when load resistor 92 is not bypassed. The contrast with the case in which load resistor 92 is not bypassed is best illustrated in FIG. 4B in which the output scale is expanded. As shown in FIG. 4B, although the output returns to approximately the baseline output in less than one second when load resistor 92 is bypassed, it takes many seconds for the output to return to the baseline output when load resistor 92 is not bypassed. The 56Ω load resistor 92 was restored in the circuit, and the sensor returned to normal operation, at a time of less than 1 second from the initiation of the test procedure. FIGS. 5A and 5B illustrate similar results with an application of a test potential difference of +10 mV for $1/64^{th}$ of a second.

Figure 6:
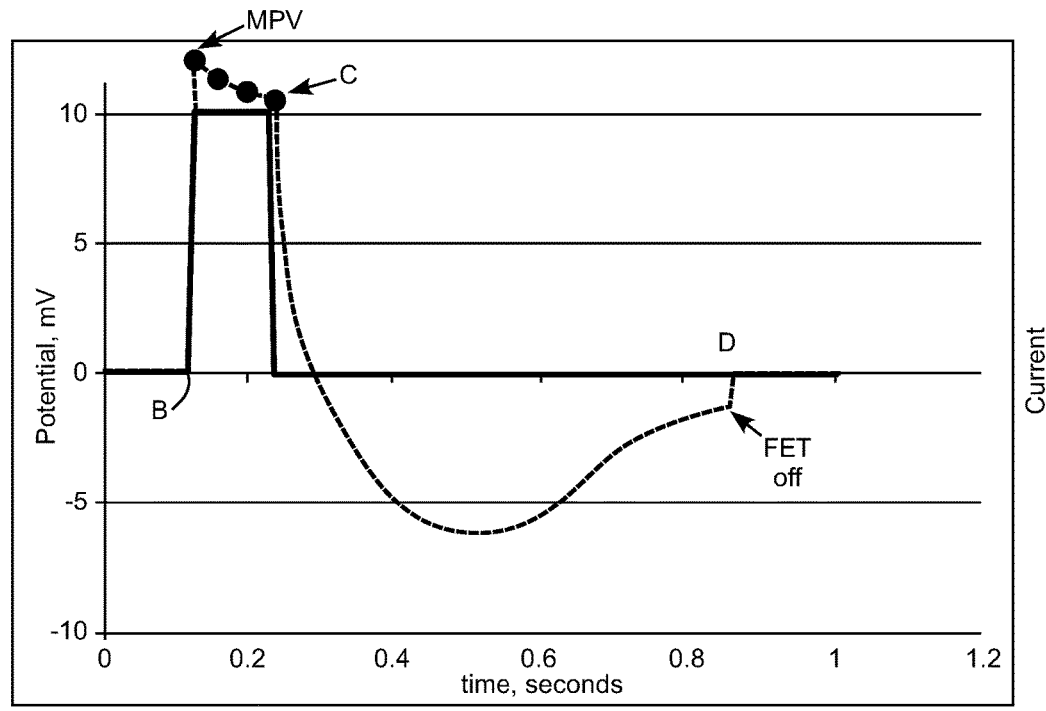
FIG. 6 illustrates the output of a sensor hereof in response to a +10 mV test potential difference wherein an FET switch is activated after the measured peak value of output (MPV), but prior to collection of number of additional data points.

FIG. 6 illustrates another embodiment of a sensor interrogation methodology hereof. In that regard FIG. 6 illustrates the output of a sensor hereof in response to a +10 mV test potential difference lasting for approximately $1/16^{th}$ of a second. In this embodiment, FET 94a is applied $3/64^{th}$ of a second after the measured peak value of output (MPV), but prior to collection of a number of additional data points. At point B, the potential is increased from 0 mV to +10 MV. The measured maximum peak value and a small portion of the positive decay curve are recorded. At point C, the FET is activated and the potential is returned to 0 mV. The current is then allowed to decay to near zero. This methodology allows more sensor data to be retrieved before FET 94a is activated while reducing the accumulated charge compared to techniques in which an increased potential is applied for, for example, 5-10 seconds. The smaller accumulated charge hereof translates into a shorter recovery time, but provides significant information regarding the state/health of the sensor. The measured peak value, the slope of the decay curve, the positive area under curve (+AUC) of the abbreviated decay curve, and the negative area under curve (−AUC) of the current discharge during FET activation are among the parameters that may collected. More data may be collected and potentially used for sensor interrogation while shortening the recovery time.

Figure 7:
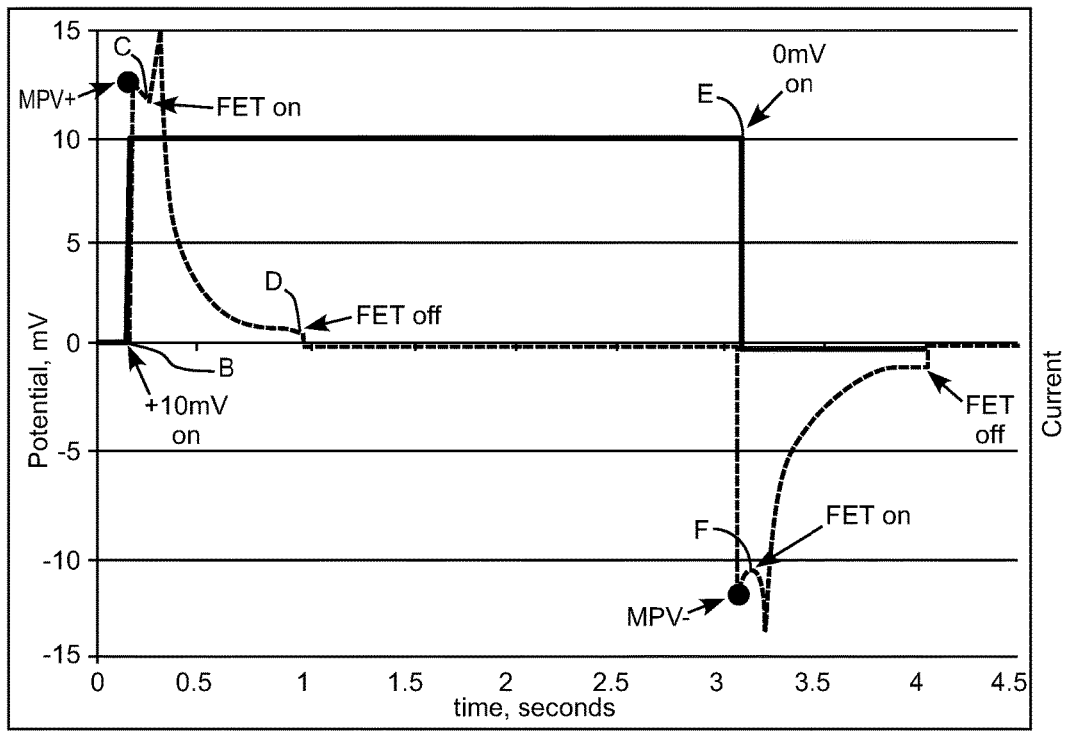
FIG. 7 illustrates the output of a sensor hereof wherein an applied potential is toggled between lower and higher values over two interrogations cycles (a "low" interrogation cycle and a "high" interrogation cycle).

FIG. 7 illustrates another embodiment of a methodology hereof in which an applied potential is toggled between lower and higher values over two interrogations cycles (a "low" interrogation cycle and a "high" interrogation cycle). In the method of FIG. 7, a positive potential step is applied at point B (for example, from 0 mV to +10 mV) during the first of two interrogation cycles. Data collected may include the positive measured peak value as well as the nature of the abbreviated decay curve. FET 94a is activated at point C. However, the potential is not returned to the original potential at point C, but is maintained at the increased potential initiated at point B. Activating FET 94a quickly discharges the curve from the positive step initiated at point B. FET 94a is de-activated at point D, before the sensor/instrument resumes operation at the increased potential established at point B (for example, +10 mV). Thus, the sensor's operating potential is now at a higher positive from its original potential (0 mV for instance), even after the sensor has returned to normal gas detection operation. The sensor performs nominally as long as the original potential is chosen to be within a plateau region wherein small changes in potential do not significantly change sensor performance. At the initiation of the second interrogation at point E, the potential is toggled back to the original value (for example, 0 mV). The resultant negative response is characterized to draw data regarding sensor state/health. Once again, data collected may include the negative measured peak value as well as the nature of the abbreviated decay curve. FET 94a is activated at point F and data is collected in the same manner as described above. However, the current direction is opposite in polarity.

In addition to the collected data described above, additional information may, for example, be obtained by comparing the positive and negative responses (MPV+vs. MPV−, AUC+vs. AUC−, slope of decay+vs. slope of decay−). A similar toggling approach may be applied to the representative examples described in connection with FIGS. 2A through 5B. In the case of those representative embodiments, the FET may be activated immediately after the MPV is taken and the data available would include the MPV+ and the MPV−.

Figure 8:
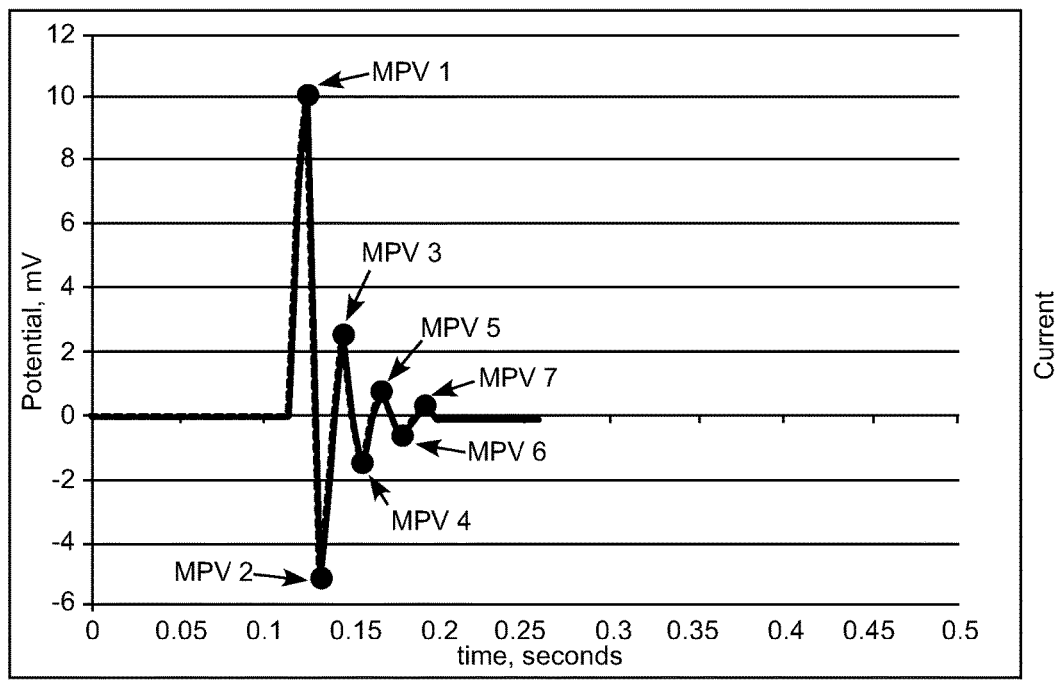
FIG. 8 illustrates the output of a sensor hereof wherein a series of potential step changes is applied to discharge the current, and wherein each consecutive potential step change is of a smaller magnitude and opposite polarity than the previous one.

Actions other than decreasing resistance may be taken to rapidly discharge current arising from, for example, a change in potential. FIG. 8, for example, illustrates a representative example in which a series of potential step changes is applied to discharge the current. In this example, each consecutive potential step change is of a smaller magnitude and opposite polarity than the previous one. This process occurs until the potential steps are so small that the resulting current has returned to approximately zero. With each consecutive step change in potential, the current is driven in the opposite direction from the previous step, and the potential may, for example, be changed to the next potential when the current is measured to be approximately zero.

In the representative example of FIG. 8, the potential is altered with very fast pulses and only the MPV's are collected. Both the positive and negative MPV's may be collected. Sensor data may be collected and relationships analyzed. For example, one may analyze all of the MPV+ values and determine changes over time to predict sensor health.

Figure 9:
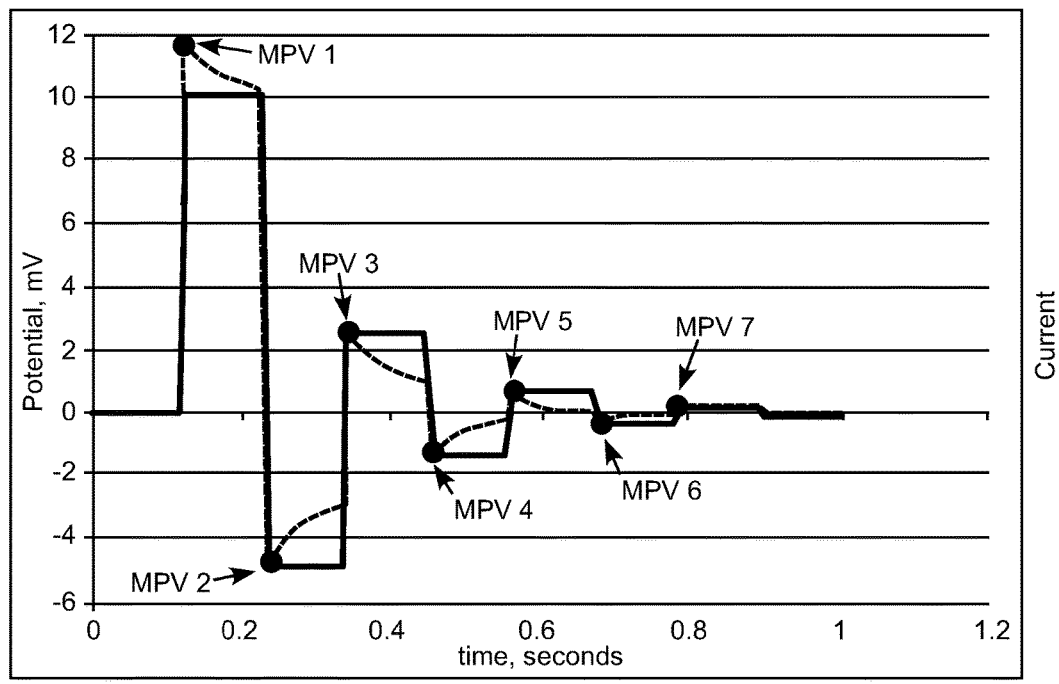
FIG. 9 illustrates the output of a sensor hereof wherein longer pulses of potential change than applied in FIG. 8 are applied so that data from abbreviated decay curves may be collected.

In the example of FIG. 9, longer pulses of potential change than applied in the representative example of FIG. 8 are applied. MPV's and AUC's of abbreviated decay curves may be collected (as discussed in connection with FIG. 7). Further, the relationships between these values over time may be used as sensor state/health predictors.

Additionally, in either of the representative examples of FIGS. 8 and 9, one may calculate a magnitude and duration of the subsequent pulse from the information obtained in the previous pulse. In such an embodiment, instead of having a series of potential steps with predetermined magnitudes and durations, the system calculates, in real time, an improved or optimized sequence with the goal of more quickly dissipating the current. In this approach, the information from only the first potential step would typically be used as a predictor of sensor state/health as the first potential step would be the only one guaranteed to be the same between interrogation events. Once again, the subsequent pulses may be optimized in real time with the sole purpose of rapidly discharging the current. As such, the subsequent potential step pulses will be variable over time, potentially making it difficult to predict sensor performance from responses thereto.

Figure 10:
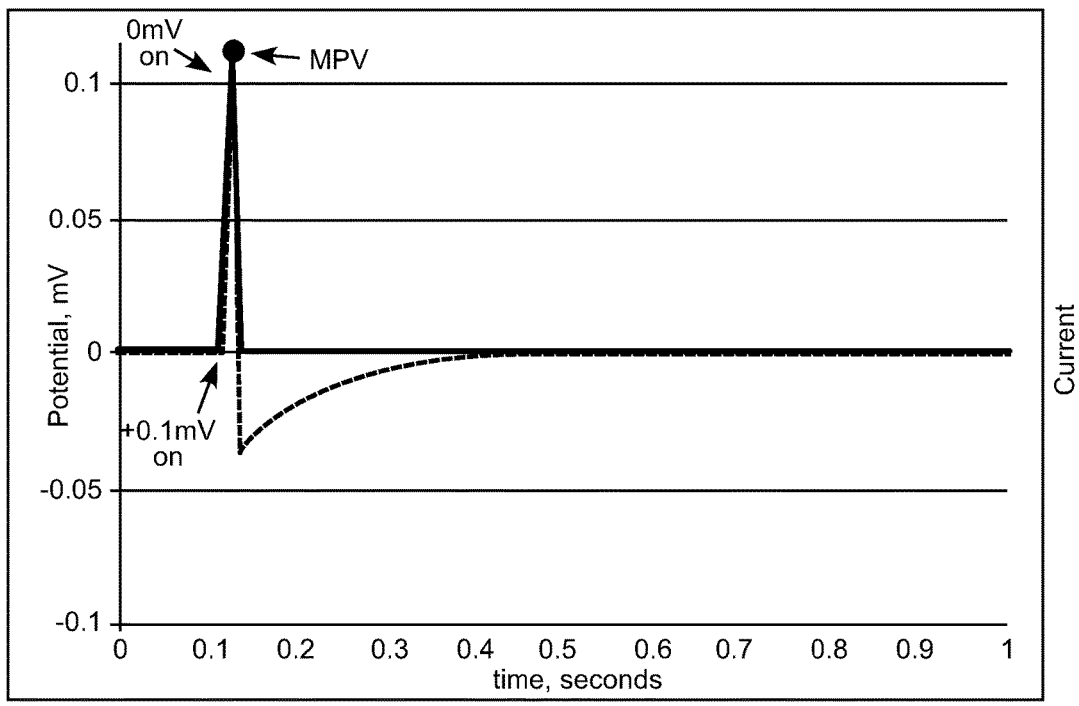
FIG. 10 illustrates the output of a sensor hereof wherein a potential step change or a pulse of sufficiently small magnitude and short duration is applied such that active control of the electronic circuitry of the sensor is not required to dissipate the current spike in less than, for example, 1 second.

As described above, instrument polling rates are currently designed to be approximately 1 second. It is unlikely in the vast majority of situations that future instruments will be designed to sample faster that 1 second per data point. Continued advances in electronics (such as integrated circuit or ASIC design) allow for further optimizing sensor interrogation parameters. Such optimization allows faster interrogation by, for example, using pulses of smaller magnitudes and shorter durations than described in the above examples (see, for example, FIG. 10). As the pulse amplitude/height (that is, potential step) gets smaller and the pulse duration gets shorter, the amount of charge that is produced during the interrogation is reduced and, consequently, the time required to recover is reduced. Active control of electronic circuitry of the sensor, such as via reduction of resistance (for example, using a FET), to dissipate charge may not be needed.

Figure 11:
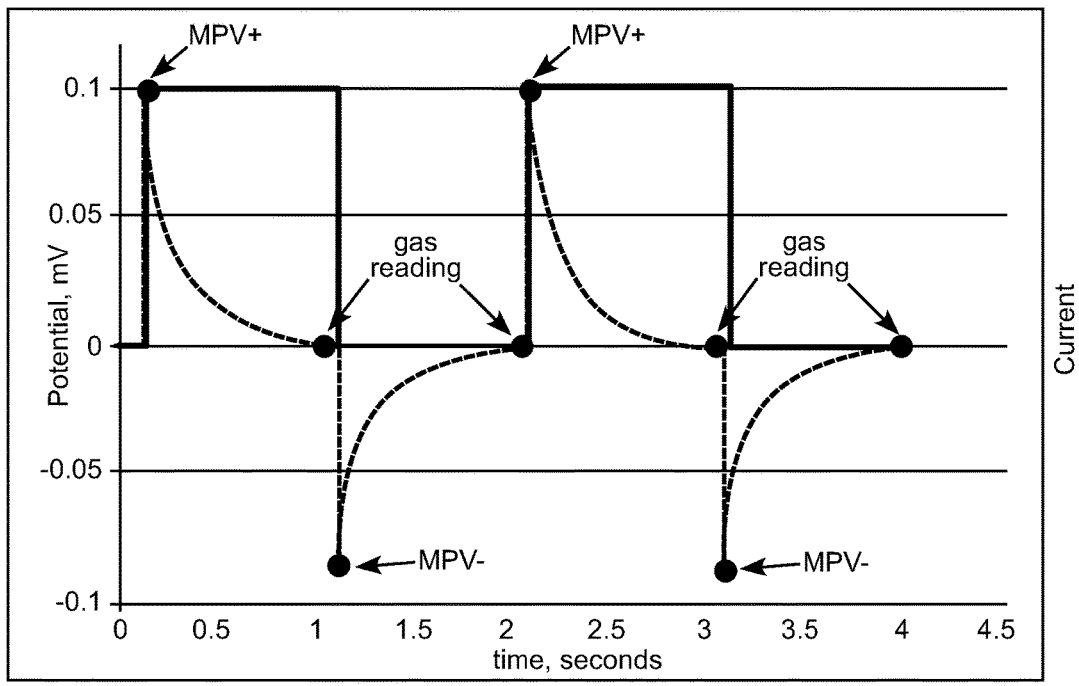
FIG. 11 illustrates the output of a sensor hereof wherein a series of potential step changes or pulses of a magnitude and duration as described in connection with FIG. 10 are applied, but instead of applying a potential perturbation as a separate interrogation event, a potential waveform is applied across the sensor, and data points are sampled at predetermined intervals within a cycle.

Instead of applying a potential perturbation as a separate interrogation event, a potential waveform may be constantly applied across the sensor, and data points may be sampled at predetermined intervals within a cycle (see FIG. 11). This waveform may, for example, be a step function. However, other waveforms may be used (for example, a sine wave, a triangle wave, etc.). This methodology is a variation of FIG. 10. In that regard, the magnitudes and duration of the potential steps are of small enough magnitude and short enough duration to allow the current to discharge quickly. Data/Information may be collected at predetermined intervals during the potential waveform. For example, MPV's, AUC's and normal (analytical) gas readings may be taken at the same time during each cycle.

In a number of embodiments, described above, a short circuit was created via a FET to quickly dissipate charge. In a number of embodiments, one may, at the same time as activation of a FET or separately from activation of a FET/switch, apply a pulse in the opposite direction of a determined magnitude to pull off the original charge that was applied minus any loss of charge. The amount of charge can be readily determined by a person skilled in the electrical arts given the proper context. This result may also be accomplished with a current pulse rather than a voltage pulse.

In a number of embodiments hereof, current is measured during a pulse and compared to a previously determined, calibrated value as described above. The calibrated value is determined during the last gas calibration (that is, at the time of manufacture and at subsequent gas calibrations of an instrument). Comparison of the calibrated value and the measured value not only provides a measurement of the state of the sensor, but also provides a means to adjust sensor output (for example, to correct for the sensor sensitivity). In a number of representative embodiments of systems, devices and/or methods hereof an internal, electronic check or interrogation of sensor functionality, connection, may be made as described herein (without the application of an analyte gas or a simulant therefor) and sensor output may be corrected as, for example, described in U.S. Pat. No. 7,413,645, the disclosure of which is incorporated herein by reference. A correction factor applied to sensor output may, for example, have the mathematical form:

$$S_C = \left(1 + \left(\frac{R_i - R_0}{R_0}\right)a\right)S_i$$

In the above equitation, $S_C$ is the corrected sensitivity of the sensor, $R_0$ and $S_0$ were the initial values of response function and sensitivity, respectively, $R_i$ and $S_i$ were the response function and sensitivity, respectively, at any point in time during the experiment, and a was an adjustable parameter. The form of this equation is not unique; other correction functions may be used as well. The application of this correction factor to the experimental data brought the indicated response of the instrument back into the specified range over the entire course of the experiment, thereby eliminating the need to recalibrate the sensor against a known standard calibration gas.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of operating an amperometric electrochemical gas sensor to detect an analyte in an environment, the sensor including a working electrode and circuitry in operative connection with the working electrode, the method comprising: performing a sensor interrogation cycle comprising applying a first pulse of electrical energy to the working electrode to generate a non-faradaic current, measuring a response to the generation of the non-faradaic current to determine a state of the sensor, and actively controlling the circuitry after an end of the first pulse of electrical energy and prior to the non-faradaic current dissipating to decrease an amount of time required to dissipate the non-faradaic current to a baseline output at which an analytic response of the sensor can be monitored to detect the analyte, wherein actively controlling the circuitry comprises decreasing a load resistance in electrical connection with the working electrode.

2. The method of claim 1 wherein the sensor Interrogation cycle lasts less than one second.

3. The method of claim 2 wherein decreasing a load resistance in electrical connection with the working electrode is via a switch.

4. The method of claim 1 wherein applying a first pulse electrical energy to the working electrode comprises changing the potential of the working electrode for a period of time.

5. The method of claim 4 wherein decreasing the load resistance occurs at the same time or after measuring the response.

6. The method of claim 4 wherein the period of time is no greater than ½ seconds.

7. The method of claim 4 wherein the period of time is no greater than 1/16 seconds.

8. The method of claim 4 wherein the period of time is no greater than 1/64 seconds.

9. The method of claim 4 wherein the sensor comprises a load resistor and a bypass switch to bypass the load resistor.

10. The method of claim 9 wherein the bypass switch comprises a field effect transistor switch, wherein activating the field effect transistor switch decreases the load resistance and deactivating the field effect transistor switch increases the load resistance.

11. The method of claim 2 further comprising periodically initiating the sensor interrogation cycle.

12. The method of claim 2 further comprising adjusting an output of the sensor at least in part on the basis of the sensor Interrogation cycle.

13. An amperometric electrochemical sensor operable to detect an analyte in an environment during an operational mode of the sensor, the sensor, comprising:
a working electrode, and circuitry in operative connection with the working electrode, the circuitry adapted to carry out an electronic interrogation cycle, the circuitry comprising a power source via which a first pulse of electrical energy is applied to the working electrode during the electronic interrogation cycle to generate a non-faradaic current, a system to measure a response of the sensor, and a control system to actively control the circuitry after an end of the first pulse of electrical energy and prior to the non-faradaic current dissipating to decrease an amount of time required to return the sensor to a baseline output at which an analytic response of the sensor can be monitored to detect the analyte, wherein actively controlling the circuitry comprises decreasing a load resistance in electrical connection with the working electrode.

14. The electrochemical sensor of claim 13 wherein the circuitry is adapted to complete the sensor interrogation cycle in less than one second.

15. The electrochemical sensor of claim 14 wherein the control system decreases the load resistance in electrical connection with the working electrode to dissipate the non-faradaic current via a switch.

16. The electrochemical sensor of claim 15 wherein applying the first pulse of electrical energy to the working electrode comprises changing the potential of the working electrode for a period of time.

17. The electrochemical sensor of claim 15 wherein decreasing the load resistance occurs at the same time or after measuring the response.

18. The electrochemical sensor of claim 16 wherein the period of time is no greater than ½ seconds.

19. The electrochemical sensor of claim 16 wherein the period of time is no greater than 1/16 seconds.

20. The electrochemical sensor of claim 16 wherein the period of time is no greater than 1/64 seconds.

21. The electrochemical sensor of claim 15 wherein the circuitry comprises a load resistor and a bypass switch to bypass the load resistor.

22. The electrochemical sensor of claim 21 wherein the bypass switch comprises a field effect transistor switch, and wherein activating the field effect transistor switch decreases the load resistance and deactivating the field effect transistor switch increases the load resistance.

23. The electrochemical sensor of claim 14 wherein the circuitry is adapted to periodically initiate the sensor interrogation cycle.

24. The electrochemical sensor of claim 14 wherein the control system is further adapted to adjust an output of the sensor at least in part on the basis of the sensor interrogation, cycle.

25. A method of operating an amperometric electrochemical gas sensor to detect an analyte in an environment, the sensor including a working electrode and circuitry in operative connection with the working electrode, the method comprising: performing a sensor interrogation cycle comprising applying a first pulse of electrical energy to the working electrode to generate a non-faradaic current, measuring a response to the generation of the non-faradaic current to determine a state of the sensor, and actively controlling the circuitry after an end of the first pulse of electrical energy and prior to the non-faradaic current dissipating to decrease an amount of time required to dissipate the non-faradaic current to a baseline output at which an analytic response of the sensor can be monitored to detect the analyte, wherein actively controlling the circuitry comprises applying at least a second pulse of electrical energy to the working electrode which is smaller in amplitude than the first pulse of electrical energy and of opposite polarity to the first pulse of electrical energy.

26. The method of claim 25 wherein the sensor interrogation cycle lasts less than one second.

27. The method of claim 26 wherein applying the first pulse of electrical energy to the working electrode comprises applying a first potential difference to the working electrode and actively controlling the circuitry comprises applying at least a second potential difference to the working electrode which is smaller in amplitude than the first potential difference and of opposite polarity to the first potential difference.

28. An amperometric electrochemical sensor operable to detect an analyte in an environment during an operational mode of the sensor, the sensor, comprising: a working electrode, and circuitry in operative connection with the working electrode, the circuitry adapted to carry out an electronic interrogation cycle, the circuitry comprising a power source via which a first pulse of electrical energy is applied to the working electrode during the electronic interrogation cycle to generate a non-faradaic current, a system to measure a response of the sensor, and a control system to actively control the circuitry after an end of the first pulse of electrical energy and prior to the non-faradaic current dissipating to decrease an amount of time required to return the sensor to a baseline output at which an analytic response of the sensor can be monitored to detect the analyte, wherein actively controlling the circuitry comprises applying at least a second pulse of electrical energy to the working electrode which is smaller in amplitude than the first pulse of electrical energy and of opposite polarity to the first pulse of electrical energy.

29. The amperometric electrochemical sensor of claim 28 wherein the circuitry is adapted to complete the sensor interrogation cycle in less than one second.

30. The amperometric electrochemical sensor of claim 29 wherein the circuitry is adapted to apply the first pulse of electrical energy comprising a first potential difference to the working electrode and the control system actively controls the circuitry to apply at least the second pulse of electrical energy comprising a second potential difference to the working electrode which is smaller in amplitude than the first potential difference and of opposite polarity to the first potential difference to dissipate the non-faradaic current.

* * * * *